United States Patent [19]

Ashihara et al.

[11] Patent Number: 5,603,898
[45] Date of Patent: *Feb. 18, 1997

[54] DRY-TYPE ANALYTICAL ELEMENT FOR IMMUNOASSAY

[75] Inventors: Yoshihiro Ashihara, Tokyo; Yukio Sudo, Saitama; Isao Nishizono, Tokyo; Toshikage Hiraoka, Saitama; Tetsuji Tanimoto, Tokyo; Shigeki Kageyama, Saitama, all of Japan

[73] Assignees: Fujirejiro Inc., Tokyo; Fuji Photo Film Co., Ltd., Kanagawa, both of Japan

[*] Notice: The portion of the term of this patent subsequent to Mar. 3, 2009, has been disclaimed.

[21] Appl. No.: 993,964

[22] Filed: Dec. 17, 1992

Related U.S. Application Data

[63] Continuation of Ser. No. 742,453, Aug. 15, 1991, abandoned, which is a continuation of Ser. No. 251,109, Sep. 29, 1988, abandoned.

[30] Foreign Application Priority Data

Sep. 30, 1987 [JP] Japan .................................. 62-243849
Oct. 26, 1987 [JP] Japan .................................. 62-268228

[51] Int. Cl.$^6$ .......................... G01N 21/00; G01N 33/53; C12M 1/14; C07K 16/00
[52] U.S. Cl. .......................... 422/57; 422/56; 422/68.11; 422/69; 422/70; 422/99; 436/510; 436/514; 436/541; 435/7.1; 435/287.2; 435/287.7; 530/387.1; 530/389.1; 530/391.1
[58] Field of Search .................................. 422/57, 58, 56, 422/50, 55, 68.1, 69, 70, 82.05, 99, 101; 435/7.1, 287, 310, 969, 970, 972; 436/510, 514, 518, 177, 178; 530/387.1, 389.1, 391.1, 810

[56] References Cited

U.S. PATENT DOCUMENTS

| | | | |
|---|---|---|---|
| 3,992,158 | 11/1976 | Przybylowicz et al. | 23/253 |
| 4,292,272 | 9/1981 | Kitajima et al. | 422/57 |
| 4,321,364 | 3/1982 | McCleary. | |
| 4,613,567 | 9/1986 | Yasoshima et al. | 435/7 |
| 4,621,048 | 11/1986 | Ashihara et al. | 435/5 |
| 4,649,105 | 3/1987 | Kasahara et al. | 435/5 |
| 4,692,404 | 9/1987 | Ashihara et al. | 435/5 |
| 4,757,001 | 7/1988 | Ashihara et al. | 435/7 |
| 5,093,081 | 3/1992 | Sudo et al. | 422/56 |
| 5,266,460 | 11/1993 | Sudo et al. | 435/7.9 |
| 5,317,089 | 5/1994 | Adolf | 530/351 |

FOREIGN PATENT DOCUMENTS

| | | |
|---|---|---|
| 0254117 | 1/1988 | European Pat. Off. . |
| 2377630 | 11/1978 | France . |
| 2017908 | 10/1979 | United Kingdom . |
| 2052057 | 1/1981 | United Kingdom . |
| 2085159 | 4/1982 | United Kingdom . |
| 00391 | 2/1983 | WIPO . |

Primary Examiner—Stephanie W. Zitomer
Assistant Examiner—Bradley A. Sisson
Attorney, Agent, or Firm—McAulay Fisher Nissen Goldberg & Kiel, LLP

[57] ABSTRACT

A dry-type analytical element for immunoassay having at least one water-permeable layer for measuring a ligand in a sample according to enzyme immunoassay, which comprises, (A) a water-soluble macromolecular substrate, and (B) an enzyme conjugated with antibody reacting with the ligand in the sample capable to act on the above water-soluble macromolecular substrate. The above analytical element further comprises, (C) a macromolecular antigen which is a conjugate of the ligand or its derivative with a macromolecular compound in the above water-permeable layer of the above dry-type analytical element.

The invention can conduct highly sensitive and simple enzyme immunoassay.

16 Claims, 1 Drawing Sheet

DRY-TYPE ANALYTICAL ELEMENT FOR IMMUNOASSAY

This is a continuation of application Ser. No. 07/742,453, filed Aug. 5, 1991, now abandoned which, in turn, is a continuation of application Ser. No. 07/251,109, filed Sep. 29, 1988, now abandoned.

BACKGROUND OF THE INVENTION

1. Field of the Invention

This invention relates to an immunologically useful dry-type analytical element for immunoassay according to enzyme immunoassay utilizing antigen-antibody reaction.

2. Description of the Prior Art

Various methods are known for determining biochemical substances contained in a body fluid or the like, and among them, enzyme immunoassay is known as a method capable of measuring them in a relatively high sensitivity. Or the other hand, the method of using a dry-type analytical element has also been developed in view of simplicity and rapidity (U.S. Pat. No. 4,292,272, Japanese Patent KOKAI Nos. 53888/1974, 102388/1984, etc.). It has been desired to develop the dry-type analytical element for immunoassay eliminating both disadvantages of dry-type analytical element method and enzyme immunoassay by combining them. Thereupon, the inventors tried to incorporate the enzyme immunoassay using a water-insoluble macromolecular substrate as the substrate for an enzyme-antibody conjugate described in Japanese Patent KOKAI Nos. 80049/1986 and 80050/1986 into dry-type analytical element. However, troubles often occurred in incorporating the water-insoluble macromolecular substrate into dry-type analytical element, and consequently, the results were not satisfactory. The inventors further investigated, and found that, the aforementioned problems has been remarkably improved by using a water-soluble macromolecular substrate as the substrate of the enzyme-antibody conjugate.

SUMMARY OF THE INVENTION

An object of the invention is to provide a dry-type analytical element for immunoassay capable of conducting an enzyme immunoassay in a high sensitivity by a simple operation.

The above object has been achieved by a dry-type analytical element for immunoassay having at least one water-permeable layer for measuring a ligand in a sample according to enzyme immunoassay, which comprises, (A) a water-soluble macromolecular substrate, and (B) an enzyme-antibody conjugate of an enzyme capable of acting on the above water-soluble macromolecular substrate with an antibody reacting with the ligand in the sample.

The above object has also been achieved by a dry-type analytical element further containing (C) a macromolecular antigen which is a conjugate of the ligand or its derivative with a macromolecular compound in the above water-permeable layer of the above dry-type analytical element.

DETAILED DESCRIPTION OF THE INVENTION

Figure 1:
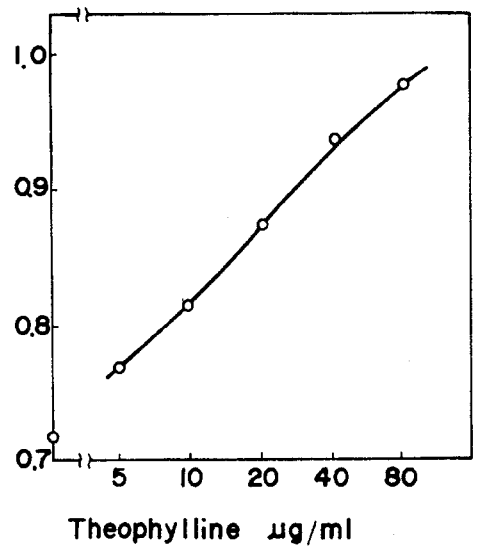
FIG. 1 indicates a calibration curve of the dry-type analytical element for immunoassay for the analysis of theophylline in Example 1.

Substances to be analyzed (analytes) of the dry-type analytical element for immunoassay of the invention is a ligand having an antigenic determinant contained in a sample. The kind of the sample is not limited, and includes blood such as whole blood, blood plasma and blood serum, lymph and urine. In the case of blood plasma, blood serum, lymph and urine, a special pretreatment is usually not necessary, and the sample may be measured as it is.

The ligand has one or more antigenic determinants, and includes various antigens existing in organs, blood or urine, such as medicinal substances including digoxin, theophylline, phenobarbital, phenytoin, penicillin and amikacin, hormones derived various endocrine glands including prostaglandin, testosterone, progesterone and thyroxin, plasma proteins including immunoglobulin, albumin and ferritin, viral antigens including HB antigen, bacteria, α-fetoprotein, cancer-relating antigens and the like. The dry-type analytical element for immunoassay of the invention is particularly effective for measuring a high molecular weight ligand, for example, having a molecular weight of more than 20,000. However, a low molecular weight ligand, for example, having a molecular weight of less than 20,000 can be measured by incorporating the macromolecular antigen which is a conjugate of the ligand or its derivative with a macromolecular compound.

When the macromolecular antigen is incorporated, the antibody composing the enzyme-antibody conjugate reacts competitively with an antigenic determinant of the ligand to be measured and of the ligand on the macromolecular antigen.

The antibody to the ligand may be produced according to a known method of producing an antibody. For example, the ligand or a conjugate of the ligand and protein is injected once or several times into subcutaneous of the back, foot pad or femoral muscle of a warm-blooded animal, such as rabbit, goat, horse, guinea pig or chicken, in an amount of 0.3 to 2 mg per kg together with an adjuvant, and thereby the antibody is produced in the humoral fluid. The serum may be used as the antibody, or it may be purified according to a known purification method of antibody, i.e. immunoglobulin, from serum.

On the other hand, this antibody may be produced as a monoclonal antibody. In this case, the above ligand or conjugate is injected several times into the abdominal cavity of a mouse together with an adjuvant, and its spleen is excised. The spleen cell is fused with mouse myeloma cell by a conventional method such as by using polyethylene glycol. The hybridoma thus obtained is cultured and cloned, and the cell capable of producing the object antibody is obtained. This cell is injected into the abdominal cavity of a mouse, and multiplied. Then, ascites are collected, and the object antibody is separated from the ascites. The antibody may be its fragment, such as $F(ab')_2$, Fab' or Fab.

Subsequently, the enzyme composing the enzyme-antibody conjugate reacts with the water-soluble macromolecular substrate. It is convenient to use the enzyme of which activity can be easily measured. They include amylase, dextranase, cellulase, collagenase, mannase, protease, elastase, lipase and glucoamylase.

The water-soluble macromolecular substrate on which the enzyme acts includes substrates of the enzyme, such as starch, amylose, amylopectin and peptide, and examples of other water-soluble substrates are described in "Koso (Enzyme) Handbook" (Ed. Maruo et al, Asakura-Shoten, Tokyo, 1982) and "Seikagaku (Biochemical) landbook" (Ed. The Japanese Biochemical Society, Maruzen, Tokyo, 1980). A directly or indirectly detectable functional group or compound may be bound to the macromolecular substrate.

The binding method of the enzyme and the antibody may be selected by considering the functional groups of both substances. Such functional groups include amino groups, carboxyl groups, hydroxyl groups, thiol groups, imidazole groups phenyl groups, and the like. As to the binding method of amino groups, many methods are known such as the diisocyanate method, the glutaraldehyde method, the difluorobenzene method, the benzoquinone method, and the like. As the method of binding amino group to carboxyl group, the peptide-binding method of carboxyl group to succinimido ester, the carbodiimide method, the Woodward reagent method and the like are known. The periodate oxidation method (Nakane method) where a bridge between amino group and sugar chain forms is also utilized. In the case of utilizing thiol group, for example, a carboxyl group is first converted to a succinimido ester, and this ester group is then allowed to react with cysteine to introduce the thiol group, and both thiol groups are bound by using a thiol-reactive bifuncional cross-linking reagent such as phenylenebismaleimide. As the method of utilizing a phenyl group, the diazotization method and the alkylation method are utilized. Other than the above, a suitable method may be selected from the various methods described in "Method in Immunology and Immunochemistry" (C. A. Williams et al., Academic Press, New York, 1976) and "Koso Meneki Sokutei-ho" "(Enzyme Immunoassay)" (E. Ishikawa et al., Igaku-shoin (Japan), 1978). The molar ratio of the combination is not limited to 1:1, and suitable ratios can be selected. After the binding reaction, the enzyme-antibody conjugate produced is purified by gel filtration, ion-exchange chromatography or affinity chromatography or a combination thereof, and lyophilized, if necessary.

On the other hand, in the case that the sample caintains an enzyme of the same kind as the enzyme of the conjugate, it is preferable that an enzyme inhibitor of which the degree to inhibit the enzyme in the sample is greater than the degree to inhibit the enzyme of the conjugate is allowed to be in contact with the enzyme in the sample.

The most desirable enzyme inhibitor inacivates the enzyme contained in the sample and does not inhibit the enzyme of the conjugate. However, it is practically sufficient that the blank value does not rise through the measurment, and the enzyme activity may be recovered after the measurement, such as by the inactivation of the enzyme inhibitor. The enzyme inhibitor may inactivate the free enzyme but not the enzyme bound to the antibody. The enzyme inhibitor may be a known enzyme inhibitor having such a specificity. Besides, when the enzyme contained in the sample is injected into a foreign animal to produce the antibody to the anzyme, this antibody may also be utilized as the enzyme inhibitor. The production of the antibody may be carried out according to the method mentioned previously.

When the lowering of the enzyme activity by the ligand is insufficient in the case of measuring a high molecular weight ligand, it is preferable to use a second antibody recognizing another antigenic determinant in the same ligand different from the antigenic determinant recognized by the antibody of the conjugate. As the second antibody, for example, a mouse is immunized with an antigen to obtain monoclonal antibodies, and two or more kinds of the antibodies reacting with different antigenic determinants from each other are isolated. Then, one of the different antibodies may be used as the second antibody.

A ligand having a low molecular weight may be measured by adding the macromolecular antigen being a conjugate of the ligand or its derivative with a macromolecular compound in the water-permeable layer of the dry-type analytical element for immunoassay of the invention, containing the water-soluble macromolecular substrate and the enzyme-antibody conjugate.

The ligand for producing the macromolecular antigen has one or more antigenic determinants common to the ligand in the sample, and it is usually the same substance as the ligand in the sample. The derivative of the ligand includes the ligand to which amino group, carboxyl group, thiol group or the like is introduced, and for example, 8-propylcarboxy-theophylline is a derivative of theophylline.

Besides, the drivative of the ligand may be a derivative of a cross-reacting compound with the antibody to the ligand. For example, when the antibody to theophylline being the ligand cross-reacts with caffeine, a derivative of caffeine may be used as the derivative of theophylline.

In the macromoleular antigen, water-soluble macromolecular compounds having a molecular weight of more than 100,000 daltons are suitable as the macromolecular compound bound to the ligand or its derivative. The examples of such a macromolecular compound include polysaccharides and their derivatives such as soluble dextran, carboxymethyl dextran, dextran induced amino group and amylose, proteins such as gelatin, hemocyanin and ferritin, and polyethylene glycol. They may be sufficient to satisfy the aforementioned conditions in a bound state to the ligand or its derivative, and include, for example, a polymer of a relatively lower molecule such as bovine serum albumin.

The macromolecular antigen may also be a polymer of the ligand or its derivative. The polymerization method may be selected from the following binding methods of the ligand or its derivative to the macromolecular compound, and for example, the ligand or its derivative may be polymerized by using a bifunctional cross-linking reagent such as carbodiimide, glutaraldehyde or the like.

The binding method of the ligand or its derivative to the macromolecular compound may be selected by considering the functional groups of both substances. Such functional groups include amino groups, carboxyl groups, hydroxyl groups, thiol groups, imidazole groups, phenyl groups and the like, and the binding method of these groups may be selected from the aforementioned methods for binding the enzyme to the antibody. The molar ratio of the combination is not limited ot 1:1, and suitable ratios can be selected. After the binding reaction, the conjugate produced is purified by gel filtration, ion-exchange chromatography, affinity chromatography or a combination thereof, and lyophilized, if necessary.

The dry-type analytical element of the invention may have similar layer compositions to various known dry-type analytical element, such as a multilayer composition containing not only the porous layer and the reagent layer described later but also a support, a spreading layer, a registration layer, a light-blocking layer, a binding layer, a filtering layer, a water-absorption layer, an under coat layer and the like. The examples of the analytical element having such a layer composition are disclosed, for example, in U.S. Pat. No. 3,992,158 and Japanese Patent KOKAI No. 164356/1980.

In the case of using a light-transmissibe water-impermeable support, the following layer compositions are practically applicable to the dry-type analytical element for immunoassay of the invention. However, the layer compositions are not limited to them.

(1) A spreading layer, a reagent layer and the support, superposed in this order.
(2) A spreading layer, a reagent layer, a registration layer and the support, superposed in this order.
(3) A spreading layer, a light-reflecting layer, a reagent layer and the support, superposed in this order.
(4) A spreading layer, a light-reflecting layer a reagent layer, a registration layer and the support, superposed in this order.
(5) A spreading layer, a reagent layer, a light-reflecting layer, a registration layer and the support, superposed in this order.
(6) A spreading layer, a first reagent layer, a light-reflecting layer, a second reagent layer and the support, superposed in this order.
(7) A spreading layer, a first reagent layer, a light-reflecting layer, a second reagent layer, a registration layer and the support, superposed in this order.
(8) A reagent-containing spreading layer, a registration layer and the support, superposed in this order.
(9) A reagent-containing spreading layer, a light-reflecting layer, a registration layer and the support superposed in this order.

In the above layer compositions (1) to (5), the reagent layer may be composed of plural different layers. Besides, the reagent layer may be an immunoassay reagent layer containing the component(s) reacting as an immunological reaction. A water-absorption layer may be interposed between the reagent layer or the registration layer and the support. In the above layer compositions (1) to (3) and (6), a filtering layer may be interposed between the reagent layer and the spreading layer or the registration layer. In the above layer compostions (3) to (7), a litering layer may be interposed between the light-reflecting layer and the spreading layer the reagent layer or the registration layer, between the reagent layer and the registration layer, or between the spreading layer and the reagent layer. When the reagent layer is composed of two or more layers, a filtering layer may be interposed between a reagent layer and another reagent layer.

Preferred materials of the light-transmissive water-impermeable support are polyethylene terephthalate, polystyrene and the like.

In order to bind a hydrophilic layer securely, generally, an undercoat layer is provided on the support, or the surface of the support is treated with a hydrophilic treatment. Whereas, the support may be a light-reflective or light-intransmissive (opaque) film, such as a white or milky white opaque polyethylene terephthalate film containing titanium dioxide particulates or barium sulfate particulates dispersed therein.

The water-permeable layer of the dry-type analytical element of the invention may be a substantially uniform layer containing a hydrophilic polymer or a porous layer disclosed, for example, in Japanese Patent KOKAI Nos. 701635/1983, 4959/1986, 116258/1987, 138756/1987, 138757/1987, 138758/1987, etc. The hydrophilic polymer may be selected from gelatin, gelatin derivatives such as phthalated gelatin, cellulose, agarose, polyacrylamide, poly-methacrylamide, copolymers of acrylamide or methacrylamide and various vinyl monomers, and the like.

The material composing the porous layer may be filter paper, nonwoven fabric, woven fabric such as plain weave, knitted fabric such as tricot fabric, glass fiber filter paper or the like. As the spreading layer, woven fabrics and knitted fabrics are preferable among them. The woven fabrics and the like may be treated with glow discharge disclosed in Japanese Patent KOKAI No. 66359/1982. A hydrophilic polymer or a surfactant may be incorporated in the spreading layer in order to controll the spreading area, the spreading speed and the like, as disclosed in Japanese Patent KOKAI Nos. 222770/1985, 219397/1988, 112999/1988, 182652/1987.

The immunoassay reagent layer is a water-permeable layer containing a part or all of the principal components of the immunoassay reagent composition in the analytical element of the invention which are:

(A) the water-soluble macromolecular substrate (B) the enzyme-antibody conjugate of an enzyme capable of acting on the abovewater-soluble macromolecular substrate with an antibody reacting with the ligand in the sample (C) the macromolecular antigen which is a conjugate of the ligand or its derivative with a macromolecular compound.

When the analytical element of the invention contains the second antibody, this layer also contains a part or all of the second antibody. The immunoassay reagent layer may be composed of plural layers, and in this case, the above respective components may be separated into different layers.

More particularly, the dry-type analytical element of the invention may contain each of the enzyme-antibody conjugate (L1), the macromolecular antigen (L2) and the water soluble macromolecular substrate (S) in the following embodiments. The figure in the circle indicates an embodiment number.

| | ① | | | | | |
|---|---|---|---|---|---|---|
| Reagent Layer A | L1,S | | | | | |

| | ② | ③ | | | | |
|---|---|---|---|---|---|---|
| Reagent Layer A | L1, | S | | | | |
| Reagent Layer B | S | L1 | | | | |

| | ④ | | | | | |
|---|---|---|---|---|---|---|
| Reagent Layer A | L1,L2,S | | | | | |

| | ⑤ | ⑥ | ⑦ | ⑧ | ⑨ | ⑩ |
|---|---|---|---|---|---|---|
| Reagent Layer A | L1,L2, | L2,S | L1,S | S | L1 | L2 |
| Reagent Layer B | S | L1 | L2 | L1,L2, | L2,S | L1,S |

| | ⑪ | ⑫ | ⑬ | ⑭ | ⑮ | ⑯ |
|---|---|---|---|---|---|---|
| Reagent Layer A | S | S | L1 | L1 | L2 | L2 |
| Reagent Layer B | L1 | L2 | S | L2 | L1 | S |
| Reagent Layer C | L2 | L1 | L2 | S | S | L1 |

In every embodiment, a spreading layer may be provided on the opposite side of the reagent layer to the support, or the spreading layer may be combined with the reagent layer. Another reagent layer containing one or more reagents other than L1, L2 and S, such as a coloring reagent, may be incorporated in any of the above embodiments ① to ⑯.

The reagent layer may contain a buffer such as a carbonate, a borate, a phosphate, Good's buffer described in Biochemistry, vol. 5, No. 2, pp 467–477 (1966) or the like. The buffer may be selected in the light of "Tanpakushitsu Koso no Kisojikken-Ho (Fundamental Experimentation Method of Proteins, Enzymes)" (Authers: Horio et al, Nankodo, 1981), the above Biochemistry reference, etc.

In the case of using the porous layer as the spreading layer, the porous layer preferably has a metering action being that a sample spotted on the spreading layer spreads at a fixed amount per unit area without uneven distribution of any component in the sample in lateral directions.

A binding layer may be provided on a reagent layer, a light-blocking layer, a filtering layer, a water-absorption layer, a registration layer or the like, in order to bind a porous layer. The binding layer is preferably composed of a hydrophilic polymer capable of binding a porous layer, when the polymer is in swollen state, such as gelatin, gelatin derivatives, polyacrylamide or starch.

The light-reflecting layer blocks the color of the sample spotted on a spreading layer, particularly the red color of hemoglobin in a whole blood sample, when the optically detectable change, such as, coloration or discoloration, occurring in a reagent layer, a registration layer or the like is measured by reflection photometry from the opposite side of the spreading layer. In addition, it also functions as a background layer. The light-reflecting layer is preferably a water-permeable layer composed of a hydrophilic polymer as a binder wherein light-reflecting particles, such as, titanium dioxide or barium sulfate are dispersed. Preferable hydrophilic polymers are gelatin, gelatin derivatives, polyacrylamide, starch and the like.

The light-reflecting particles may also be incorporated into a spreading layer, a reagent layer, a registration layer or the like in addition to or instead of the light-reflecting layer.

The analytical element of the invention can be prepared according to a known method described in the foregoing patents.

The integral multilayer analytical element of the invention is preferably cut into square pieces having a side of about 15 mm to about 30 mm or circular pieces having a similar size or the like, and put in a slide frame disclosed in U.S. Pat. No. 4,169,751, Japanese Patent KOKAI No. 63452/1982, U.S. Pat. No. 4,387,990 and Japanese Utility Model KOKAI No. 32350/1983, U.S. Pat. No. 4,169,751, U.S. Pat. No. 4,387, 990, PCT application WO 83/00391, etc. This analytical slide is preferable in view of production, packaging, transportation, stock, measuring operation and the like. While, the analytical element may be supplied in a form of a long tape packaged in a cassette or a magazine or in a form of small pieces stuck on or placed in a card having an opening.

The measurement is carried out, for example, according to the manner disclosed in the specifications of the foregoing patents. About 5 μl to about 30 μl, preferably about 8 μl to about 15 μl of an aqueous sample, such as whole blood, blood plasma, blood serum, lymph or urine, is spotted on the spreading layer, and incubated at a definite temperature in the range of about 20° C. to about 40° C., preferably at 37° C. or its vicinity for 1 to 10 minutes, preferably 2 to 7 minutes. Thereafter, the coloration or discoloration occurred in the analytical element is measured from the side of the support through reflection photometry using the visible or ultraviolet light having the wave length of a maximum absorption or its vicinity. The ligand content of the sample is determined by the principle of colorimetry using a previously prepared calibration curve. Instead, it is also possible that a fluorescence intensity emitted from the analytical element is measured, and the ligand content of the sample is determined by using a calibration curve prepared previously. A quantitative analysis of the ligand can be conducted in a high accuracy by fixing the spotted amount of a liquid sample, the incubation time and the temperature. In the embodiment of using a light-reflecting or opaque support, the coloration or discoloration occurred in the analytical element is measured from the side of the topmost layer being the opposite side of the support through reflection photometry.

When this measurement is carried out by using the chemical-analytical apparatus disclosed in U.S. Pat. Nos. 4,488,810, 4,424,191 and 4,424,191, highly accurate results can easily be obtained by a simple operation.

EXAMPLES

Example 1

(1) Preparation of Enzyme-Antibody Conjugate i) Preparation of CHM-induced α-amylase 5 mg of Bacillus subtilis α-amylase was dissolved in 1 ml of 0.1M glycerophosphate buffer solution of pH 6.3. 100 μl of 350 mg/ml 4-maleimidomethylcyclohexane-1-carboxylic acid N-hydroxysuccinimide ester (CHMS) dimethylformamide (DMF) solution was added to this α-amylase solution, and allowed to stand at room temperature for 1 hour. The reaction mixture was introduced into a Sephadex G-25 column, and gel filtration was carried out by using 0.1M glycerophosphate buffer solution of pH 7.0. The void fractions were collected to obtain the desired CHM-induced α-amylase.

ii) Preparation of anti-theophylline mouse IgG F(ab')$_2$ 300 μg of papain was added to 2 ml of 0.1M acetate buffer solution of pH 5.5 containing 10 mg of anti-theophylline mouse IgG, and stirred at 37° C. for 18 hours. This reaction solution adjusted to pH 6.0 by adding 0.1N NaOH was introduced in an AcA-44 gel column previously equilibrated with 0.1M phosphate-buffered 1 mM EDTA solution of pH 6.3, and eluted by the above phosphate buffer solution. The peak portion eluted around the molecular weight of 100,000 was collected and concentrated to 1 ml to obtain the object anti-theophylline mouse IgG F(ab')$_2$.

iii) Preparation of α-amylase-anti-theophylline mouse IgG Fab' conjugate 1 ml of 0.1M phosphate-buffered 1 mM EDTA solution of pH 6.0 containing 6 mg of the above anti-theophylline mouse IgG f(ab')$_2$ was mixed with 100 μl of 10 mg/ml 2-mercaptoethylamine hydrochloride aqueous solution, and allowed to stand at 37° C. for 90 minutes. Gel filtration using a Sephadex G-25 column which was previously equilibrated with 0.1M glycern phosphate buffer solution of pH 7.0 was carried out, and unreacted 2-mercaptoethylamine was removed to obtain HS-Fab'. 2 mg of CHM-induced α-amylase prepared in item i) was added, and allowed to react at 37° C. for 90 minutes. Subsequently, this reaction solution was separated by gel filtration using an AcA-34 column which was equilibrated with 0.1M glycerophosphate-buffered 5 mM calcium chloride solution of pH 7.0, and the fractions corresponding to the molecular weights of greater than 200,000 were collected. The fractions were concentrated to obtain the object conjugate.

(2) Synthesis of Macromolecular Antigen (Horse Ferritin-Theophylline Conjugate)

5 mg of 8-propylcarboxytheophylline dissolved in 1 ml of dimethylformamide (DMF) was mixed with 3 mg of N-hydroxysuccinimide and 5 mg of water-soluble carbodiimide, and stirred at room temperature for 2 hours to obtain activated theophylline. 500 µl of the above activated theophylline solution was added to 10 mg of horse ferritin dissolved in 1 ml of 0.1M sodium hydrogen carbonate aqueous solution, and allowed to stand at room themperature for 1 hour. Unreacted substances were removed by using a Sephadex G-25 gel column previously equilibrated with a phosphate-buffered saline solution of pH 7.0 to obtain 9 mg of the object macromolecular antigen of horse ferritin-theophylline conjugate.

(3) Preparation of Dry-Type Analytical Element

Onto a colorless pransparent polyethylene terephthalate (PET) sheet support 180 µm thick on which a gelatin undercoat layer was provided, the following aqueous solution was applied so as to become the following coating amount, and dried to form a crosslinking agent-containing water-absorption layer.

| | |
|---|---|
| Alkali-treated gelatin | 6.6 g/m$^2$ |
| Nonylphenoxypolyglycidol (Containing 10 glycidol units on average) | 330 mg/m$^2$ |
| Bis[(vinylsulfonylmethylcarbonyl)amino]methane | 380 mg/m$^2$ |

Onto the crosslinking agent-containing water-absorption layer, the following aqueous suspension was applied so as to become the following coating amount, and dried to form a registration layer.

| | |
|---|---|
| Acid-treated gelatin | 10 g/m$^2$ |
| Polymer aqueous latex (1)* (Containing 10% of solid matter) | 3 g/m$^2$ |
| Nonylphenoxypolyglycidol (Containing 10 glycidol units on average) | 2 g/m$^2$ |

*[(p-Divinylbenzene)$_x$-(styrene)$_y$-((1-piperidininmethyl)styrene chloride)$_w$] terpolymer x:y:w = 5:47.5:47.5

Onto the registration layer, the following aqueous suspension was applied so as to become the following coating amount, and dried to form a light-blocking layer having a dry thickness of 7 µm.

| | |
|---|---|
| Alkali-treated gelatin | 2.9 g/m$^2$ |
| Ratile type titanium dioxide particulates | 13 g/m$^2$ |
| Nonylphenoxypolyglycidol (Containing 10 glycidol units on average) | 400 mg/m$^2$ |

Onto the light-blocking layer, the following aqueous solution was applied so as to become the following coating amount, and dried to form a binding layer having a dry thickness of 5/µm.

| | |
|---|---|
| Alkali-treated gelatin | 6.7 g/m$^2$ |
| Nonylphenoxypolyglycidol (Containing 10 glycidol units on average) | 600 mg/m$^2$ |

The surface of the binding layer was uniformly moistened with 30 g/m$^2$ of water, and a tricot fabric about 250 µm thick made by knitting 50 deniers PET span yarn using 36 gauge was lightly pressed almost uniformly to laminate thereon as the porous spreading layer.

Subsequently, the following aqueous solution containing a substrate and immunological reagent composition was applied onto the porous spreading layer, and dried.

| | |
|---|---|
| DyAmyl (trade name of a dye-bound starch) | 3 g/m$^2$ |
| Amylase-anti-theophylline mouse IgG Fab' | 4.0 mg/m$^2$ |
| Horse ferritin-theophylline | 4.2 mg/m$^2$ |
| Nonylphenoxypolyethoxyethanol (Containing 40 hydroxyethylene units on average) | 500 mg/m$^2$ |

The integral multilayer analytical element for immunoassay thus prepared was cut into square tips having a side of 15 mm, and each tip was placed in a slide frame disclosed in Japanese Patent KOKAI No. 32350/1983 to complete a multilayer analytical slide (1) for the analysis of theophylline.

(4) Evaluation Test

20 µl of 50 mM glycerophosphate buffer solution of pH 7 containing a known amount of theophylline was spotted onto the spreading layer of the above multilayer analytical slide (1) for the analysis of theophylline. After incubating at 37° C. for 20 minutes, the reflection optical density at 540 nm was measured from the side of the support. The results are shown in FIG. 1.

By the calibration curve of FIG. 1, it was found that the content of theophyllinethe can be determined by the dry-type analytical element for immunoassay for the analysis of theophylline accurately.

Example 2

(1) Preparation of Dry-Type Analytical Element

The crosslinking agent-containing water-absorption layer, the registration layer, the light-blocking layer and the binding layer were successively laminated on the support in the same manner as Example 1.

The surface of the binding layer was uniformly moistened with 30 g/m$^2$ of water, and a cellulose acetate membrane filter having a nominal pore size of 3.0 µm and a thickness of about 140 µm was laminated thereon.

The following aqueous solution was applied thereon to form a porous reagent layer.

| | |
|---|---|
| Amylase-anti-theophylline mouse IgG Fab' (Example (1)) | 4.0 mg/m$^2$ |
| Nonylphenoxypolyethoxyethanol | 200 mg/m$^2$ |

A tricot fabric about 250 µm thick made by knitting 50 deniers PET spun yarn using 36 gauge containing the following substrate and immunological reagent composition was laminated onto the porous reagent layer as the porous spreading layer.

| | |
|---|---|
| DyAmyl (trade name) | 3 g/m$^2$ |
| Horse ferritin-theophylline (Example 1 (2)) | 4.2 mg/m$^2$ |
| Nonylphenoxypolyethoxyethanol | 500 mg/m$^2$ |

The integral multilayer analytical element for immunoassay thus prepared was cut into square tips having a side of 15 mm, and each tip was placed in a slide frame disclosed in Japanese Patent KOKAI No. 32350/1983 to complete a multilayer analytical slide (2) for the analysis of theophylline.

(2) Evaluation Test

Figure 2:
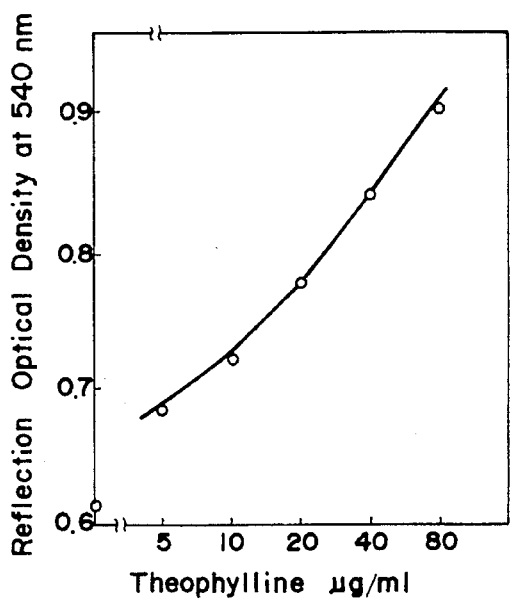
FIG. 2 indicates a calibration curve of the dry-type analytical element for immunoassay for the analysis of theophylline in Example 2.

Using the above multilayer analytical slide (2), theophylline concentration was measured in the same manner as the evaluation test of Example 1, and the results shown in FIG. 2 were obtained.

By the calibration curve of FIG. 2, it was found that the content of theophylline can be determined by the dry-type analytical element for immunoassay for the analysis of theophylline accurately.

Example 3

(1) Preparation of Enzyme-Antibody Conjugate i) Preparation of anti-human ferritin goat IgG F(ab')$_2$ 0.5 mg of pepsin was added to 2 ml of 0.1M acetate buffer solution of pH 4.2 containing 10 mg of anti-human ferritin goat IgG, and stirred at 37° C. overnight. This reaction solution adjusted to pH 7.0 by adding 0.1N NaOH was introduced in an AcA-44 gel column previously equilibrated with 0.1M phosphate-buffered 1 mM EDTA solution of pH 6.0, and eluted by the above phosphate buffer solution. The peak portion eluted around the molecular weight of 100,000 was collected and concentrated to 1 ml to obtain the object anti-human ferritin goat IgG F(ab')$_2$.

ii) Preparation of α-amylase-anti-human ferritin goat IgG Fab' conjugate 1 ml of 0.1M phosphate buffered 1 mM EDTA solution of pH 6.0 containing 6 mg of the above anti-human ferritin goat IgG F(ab')$_2$ was mixed with 100 μl of 0.1M 2-mercaptoethylamine hydrochloride aqueous aolution, and incubated at 37° C. for 2 hours. Gel filtration using a Sephadex G-25 column which was previously equilibrated with 0.1M glycerophosphate buffer solution of pit 7.0 was carried out, and unreacted 2-mercaptoethylamine was removed to obtain 5 mg of Fab'-SH. 0.62 mg of CHM-induced α-amylase prepared in Example 1(1)i) was added to the Fab'-SH solution, and allowed to stand at 4° C. overnight. Subsequently, this reaction solution was concentrated to 1 ml with PEG 20,000, and then, separated by gel filtration using a Sephacryl S-300 column which was equilibrated with 0.1M glycerophosphate-buffered 5 mM calcium chloride solution of pH 7.0. The protein fractions corresponding to the molecular weights of about 200,000 to 300,000 daltons were collected to obtain the object conjugate.

(2) Preparation of Dry-Type Analytical Element

A dry-type analytical element was prepared in the same manner as Example 1, except the sabstrate and the immunological reagent composition.

The following aqueous solution containing substrate and the immunological reagent composition was applied onto the porous spreading layer, and dried.

| | |
|---|---|
| DyAmyl (trade name) | 3.5 g/m$^2$ |
| α-amylase-anti-human ferritin goat IgG Fab' | 1 mg/m$^2$ |
| Nonylphenoxypolyethoxyethanol | 500 mg/m$^2$ |
| (Containing 40 hydroxyethylene units on average) | |

The integral multilayer analytical element for immunoassay thus prepared was cut into square tips having a side of 15 mm, and each tip was placed in a slide frame disclosed in Japanese Patent KOKAI No. 32350/1983 to complete a multilayer analytical slide (3) for the analysis of ferritin.

(3) Evaluation Test

10 μl of 50 mM glycerophosphate buffer solution of pH 7.0 containing a known amount of ferritin was spotted onto the spreading layer of the above multilayer analytical slide (3) for the analysis of ferritin. After incubating at 37° C. for 30 minutes, the reflection optical density at 540 nm was measured from the side of the support. The results are shown in FIG. 3.

Figure 3:
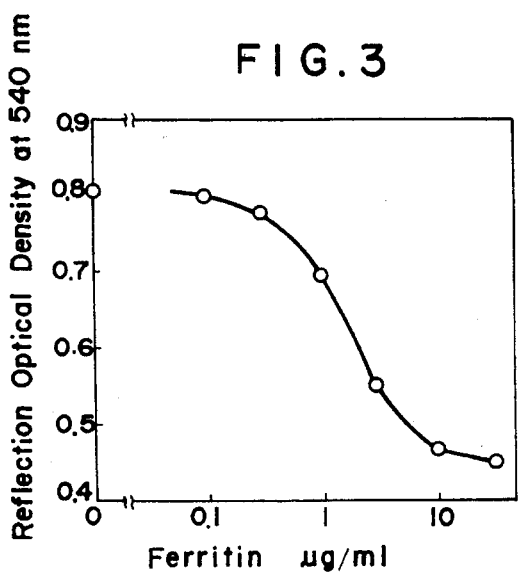
FIG. 3 indicates a calibration curve of the dry-type analytical element for immunoassay for the analysis of ferritin in Example 3.

By the calibration curve of FIG. 3, it was found that the content of ferritin can be determined by the dry-type analytical element for immunoassay for the analysis of ferritin accurately.

Example 4

(1) Preparation of Dry-Type Analytical Element

A dry-type analytical element was prepared in the same manner as Example 2, except that the following reagents were used as the reagent incorporated in the porous reagent layer and the porous spreading layer.

The following reagent composition was applied onto the porous reagent layer, and dried.

| | |
|---|---|
| DyAmyl (trade name) | 3.5 g/m$^2$ |
| Nonylphenoxypolyethoxyethanol | 100 mg/m$^2$ |
| (Containing 10 hydroxyethylene units on average) | |

The following immunological reagent composition was incorporated in the porous spreading layer.

| | |
|---|---|
| α-amylase-anti-human ferritin goat IgG Fab' (Example 3 (1)) | 2 mg/m$^2$ |
| Nonylphenoxypolyethoxyethanol | 500 mg/m$^2$ |

The integral multilayer analytical element for immunoassay thus prepared was cut into square tips having a side of 15 mm, and each tip was placed in a slide frame disclosed in Japanese Patent KOKAI No. 32350/1983 to complete a multilayer analytical slide (4) for the analysis of ferritin.

(2) Evaluation Test

Figure 4:
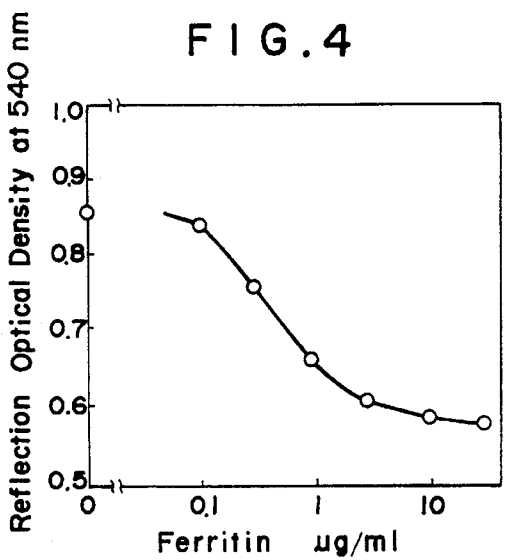
FIG. 4 indicates a calibration curve of the dry-type analytical element for immunoassay for the analysis of ferritin in Example 4.

Using the above multilayer analytical slide (4), ferritin concentration was measured in the same manner as the evaluation test of Example 3, and the results shown in FIG. 4 were obtained.

By the calibration curve of FIG. 4, it was found that the content of ferritin can be determined by the dry-type analytical element for immunoassay for the analysis of ferritin accurately.

We claim:

1. A dry-type analytical element for immunoassay comprising at least two water-permeable layers for measuring a ligand in a sample of bodily fluids according to enzyme immunoassay, said ligand having a molecular weight of more than 20,000, at least one of said water-permeable layers being a porous layer containing an immunoassay reagent composition consisting essentially of (a) a water-soluble macromolecular substrate, and (b) an enzyme-antibody conjugate wherein said enzyme is a hydrolase selected from amylase and glucoamylase capable of hydrolyzing the water-soluble macromolecular substrate with an antibody reacting with the ligand in the sample.

2. The analytical element of claim 1 which further comprises a second antibody recognizing another antigenic determinant.

3. The analytical element of claim 1 wherein said porous layer is composed of two or three layers which are adjacent to each other.

4. The analytical element of claim 3 wherein said layers are a spreading layer and a porous reagent layer.

5. The analytical element of claim 1 wherein said sample is blood, lymph or urine.

6. The analytical element of claim 1 wherein said porous layer is a spreading layer.

7. The analytical element of claim 1, wherein said ligand is ferritin.

8. The analytical element of claim 1 wherein the water-soluble macromolecular substrate is starch, amylose or amylopectin.

9. A dry-type analytical element for immunoassay comprising at least two superposed communicating water-permeable layers for measuring a ligand in a sample of bodily fluids according to enzyme immunoassay, said ligand having a molecular weight of less than 20,000, at least one of said water-permeable layers being a porous layer containing an immunoassay reagent composition consisting essentially of (a) a water-soluble macromolecular substrate, (b) an enzyme-antibody conjugate wherein said enzyme is a hydrolase selected from amylase and glucoamylase capable of hydrolyzing the water-soluble macromolecular substrate with an antibody reacting with the ligand in the sample, and (c) a macromolecular antigen which is a conjugate of the ligand or its derivative with a macromolecular compound having a molecular weight of more than 100,000 in the water-permeable layer.

10. The analytical element of claim 9 wherein said porous layer is composed of two or three layers which are adjacent to each other.

11. The analytical element of claim 10 wherein said layers are a spreading layer and a porous reagent layer.

12. The analytical element of claim 9 wherein said sample is blood, lymph or urine.

13. The analytical element of claim 9 wherein said macromolecular compound is a member selected from the group consisting of polysaccharides, soluble dextran, carboxymethyl dextran, dextran induced amino group, amylose, proteins and polyethylene glycol.

14. The analytical element of claim 9 wherein said porous layer is a spreading layer.

15. The analytical element of claim 15 wherein said ligand is theophylline.

16. The analytical element of claim 9 wherein the water-soluble macromolecular substrate is starch, amylose or amylopectin.

* * * * *